United States Patent
Zhao et al.

(10) Patent No.: US 10,823,679 B2
(45) Date of Patent: Nov. 3, 2020

(54) SCANNING TYPE LASER INDUCED SPECTRUM ANALYSIS AND DETECTION SYSTEM

(71) Applicant: Academy of Opto-Electronics Chinese Academy of Sciences, Beijing (CN)

(72) Inventors: Tianzhuo Zhao, Beijing (CN); Fuqiang Lian, Beijing (CN); Zeqiang Mo, Beijing (CN); Weiran Lin, Beijing (CN); Yang Liu, Beijing (CN); Shuzhen Nie, Beijing (CN); Hong Xiao, Beijing (CN); Hongbo Zhang, Beijing (CN); Zhongwei Fan, Beijing (CN)

(73) Assignee: Academy of Opto-Electronics Chinese Academy of Sciences, Beijing (CN)

( * ) Notice: Subject to any disclaimer, the term of this patent is extended or adjusted under 35 U.S.C. 154(b) by 0 days.

(21) Appl. No.: 16/348,041

(22) PCT Filed: Nov. 24, 2016

(86) PCT No.: PCT/CN2016/107129
§ 371 (c)(1),
(2) Date: May 7, 2019

(87) PCT Pub. No.: WO2018/082136
PCT Pub. Date: May 11, 2018

(65) Prior Publication Data
US 2019/0271652 A1 Sep. 5, 2019

(30) Foreign Application Priority Data
Nov. 7, 2016 (CN) .......................... 2016 1 0975941

(51) Int. Cl.
*G01N 21/71* (2006.01)
*G01N 33/24* (2006.01)

(52) U.S. Cl.
CPC ........... *G01N 21/718* (2013.01); *G01N 33/24* (2013.01)

(58) Field of Classification Search
CPC ................. G01N 21/718; G01N 33/24; G01N 2201/0221; G01N 21/67;
(Continued)

(56) References Cited

U.S. PATENT DOCUMENTS

| 4,311,385 | A * | 1/1982 | Keene | G01B 11/26 356/139.08 |
| 6,678,050 | B2 * | 1/2004 | Pope | G01N 21/27 356/435 |

(Continued)

FOREIGN PATENT DOCUMENTS

| CN | 101464411 A | 6/2009 |
| CN | 101984344 A | 3/2011 |

(Continued)

OTHER PUBLICATIONS

International Search Report for PCT Application No. PCT/CN2016/107129, dated Aug. 3, 2017 in 4 pages.

*Primary Examiner* — Mohamed K Amara
(74) *Attorney, Agent, or Firm* — Knobbe, Martens, Olson & Bear, LLP

(57) ABSTRACT

A scanning type laser induced spectrum surface range analysis and detection system includes a laser emitting head connected to an external laser inducing light source, which generates lasers emitted through the laser emitting head, so as to generate laser induced plasma. A focusing optical device converges induction excited laser beams emitted by the laser emitting head onto a surface of a tested sample. Then, a reflector collects wide spectral range induced plasma scattered light signals of the tested sample and converges the signals into a light collecting device. The light collecting device converges induced plasma scattered light into an
(Continued)

optical fiber and transmits the induced plasma scattered light to an external spectrograph; and the external spectrograph divides a spectrum formed by the plasma to obtain spectral strength data of different wavelengths.

7 Claims, 3 Drawing Sheets

(58) Field of Classification Search
CPC ......... G01N 2201/0833; G01N 27/628; G01N 15/0612; G01N 2001/4027; G01N 21/474; G01N 2201/0697; G01N 2201/08; G01J 3/443; G01J 3/0272; G01J 3/02; G01J 3/0208; G01J 3/0218; G01J 3/0291; G01J 3/44; G01J 3/10; G01J 3/18; G01J 3/2823; G01J 3/28; H01J 65/04; H01J 61/025; H01J 37/32321; A61B 18/20; A61B 2017/00057; A61B 2018/00636; G02B 21/06; G02B 21/082; H05H 1/24

See application file for complete search history.

(56) References Cited

U.S. PATENT DOCUMENTS

| | | | | |
|---|---|---|---|---|
| 6,762,836 B2* | 7/2004 | Benicewicz | | G01N 21/718 356/237.3 |
| 6,836,325 B2* | 12/2004 | Maczura | | G01J 3/02 356/328 |
| 7,016,035 B2* | 3/2006 | Wu | | G01J 3/02 356/318 |
| 7,092,087 B2* | 8/2006 | Kumar | | A61B 5/0075 250/461.2 |
| 7,233,643 B2* | 6/2007 | Sipila | | G01N 21/718 378/44 |
| 7,236,243 B2* | 6/2007 | Beecroft | | G01J 3/02 356/328 |
| 7,394,537 B1* | 7/2008 | Lindfors | | G01N 21/718 356/318 |
| 7,821,634 B2* | 10/2010 | Dillon | | G01J 3/02 356/318 |
| 7,912,100 B2* | 3/2011 | Shah | | G01J 11/00 372/6 |
| 8,436,991 B2* | 5/2013 | Senac | | G01J 3/0256 356/316 |
| 9,255,900 B2* | 2/2016 | Fishbine | | G01J 3/0218 |
| 2002/0148815 A1* | 10/2002 | Suzuki | | B23K 26/067 219/121.7 |
| 2003/0174325 A1* | 9/2003 | Zhang | | G01J 3/443 356/318 |
| 2005/0068524 A1* | 3/2005 | Wu | | G01J 3/02 356/316 |
| 2008/0151241 A1* | 6/2008 | Lindfors | | G01N 21/718 356/318 |
| 2010/0264820 A1* | 10/2010 | Sumitomo | | H01J 61/025 313/639 |
| 2012/0217422 A1* | 8/2012 | Yabu | | H05G 2/006 250/504 R |
| 2014/0022531 A1* | 1/2014 | Sackett | | G01J 3/0227 356/51 |
| 2014/0022532 A1* | 1/2014 | Sackett | | G01J 3/0227 356/51 |
| 2014/0204377 A1* | 7/2014 | Day | | G01J 3/443 356/318 |
| 2014/0204378 A1* | 7/2014 | Day | | G01J 3/2823 356/326 |
| 2015/0029475 A1* | 1/2015 | Shimizu | | G02B 27/48 353/98 |
| 2015/0103334 A1* | 4/2015 | Quant | | G01N 21/718 356/51 |
| 2016/0041033 A1* | 2/2016 | Oskotsky | | G01J 3/2823 356/328 |
| 2017/0268927 A1* | 9/2017 | Beardsley | | G01J 3/0208 |
| 2018/0209909 A1* | 7/2018 | Jian | | G02B 5/10 |
| 2019/0041620 A1* | 2/2019 | Mikami | | G02F 1/11 |
| 2019/0219511 A1* | 7/2019 | Sun | | G01N 21/718 |
| 2020/0049967 A1* | 2/2020 | Kessler | | G02B 21/0032 |

FOREIGN PATENT DOCUMENTS

| | | |
|---|---|---|
| CN | 102313721 A | 1/2012 |
| CN | 204330594 U | 5/2015 |
| FR | 2941529 A1 | 7/2010 |

\* cited by examiner

SCANNING TYPE LASER INDUCED SPECTRUM ANALYSIS AND DETECTION SYSTEM

CROSS-REFERENCE TO RELATED APPLICATIONS

This application is the U.S. National Phase under 35. U.S.C. § 371 of International Application PCT/CN2016/107129, filed Nov. 24, 2016, which claims priority to Chinese Patent Application No. 201610975941.6, filed Nov. 7, 2016.

FIELD OF TECHNOLOGY

The present disclosure relates to the technical field of photoelectric non-destructive testing, particularly to a scanning type laser induced spectrum surface range analysis and detection system.

BACKGROUND

Laser Induced Plasma Spectroscopy (LIPS) detection technique is an analytical technique that ablates a material with pulse lasers to generate plasma, and qualitatively or quantitatively study the composition of the material with plasma emission spectrum. It has the advantages of wide application range, fast analysis speed, small measurement destruction, remote non-contact measurement and real-time detection. The Laser Induced Plasma Spectroscopy is a quantitative analytical technique based on the emission spectrum produced by the interaction of laser and material, which requires only a few micrograms during the measurement and can provide a non-destructive measurement and the elemental analysis of any physical state material without sample pretreatment. The Laser Induced Plasma Spectroscopy can quantitatively analyze the elements in the material by calibration, and the detection limit and precision can fully meet the application requirements.

Many patents based on the elemental analysis with laser induced technology have been filed; but most of the patents are mainly application schemes and methods applied to the detections of different application fields. For example, the patent with an application number of 201510566291.5 protects an identification method for rice varieties based on laser induced breakdown spectrum; the patent with an application number of 201110360773.7 protects an online detection system which uses the laser to converge on the surface of the molten steel to obtain the compositions thereof by analyzing the excited plasma spectrum. In addition, there are some patents of laser induced detection technology that provide the signal enhancement and improvement for the laser induced technology. For example, the patent with an application number of 201510073090.1 provides an analysis system and method for two-dimensional energy-related laser induced breakdown spectrum, which can analyze the spectral characteristics more clearly and improve the detection abilities and repetition of conventional laser induced breakdown spectrum methods. The invention patent with an application number of 201480041306 discloses an elemental composition analysis method by using dual-pulse laser induced breakdown spectrometer.

The wide range scanning collection is of great value for dynamic detection and improving the detection efficiency. As for the existing laser induced breakdown spectrum detection solutions, they all have difficulties to provide a convenient wide range scanning collection of samples. For example, the patents with application numbers of 201180054843.4 and 201220330846.8, realize the laser induced breakdown spectrum analysis by the convergences of a plurality of reflectors and lenses, but can only focus in the laser axis direction and cannot realize the scanning of laser induced detection.

In addition, most of the existing patents require bidirectional spectroscopic dichroic optics (such as dichroic mirrors), that is, a device used for transmitting the light with specific wavelengths and reflecting the light with other specific wavelengths according to different wavelengths of the light. For example, the patent with an application number of 201310610554.9 protects a portable laser induced breakdown spectrum analyzer and method. The analyzer includes a dichroic mirror for transmitting of the exciting laser (normally to be the strong laser signal having a spectrum width smaller than 1 nanometer) and collecting the spectrum signal (normally to be the signal having wide spectrum and low energy signal in the hundreds of nanometers range) to divide. While in the optical processing field, processing the dichroic optics is difficult, and the reflectance is low when reflect in a wide spectral range of hundreds of nanometers, and the damage threshold of elements is 5 to 10 times lower than that of the mature single wavelength technique, which limits the important index such as energy of induced laser, signal-to-noise ratio of development equipment and stability etc. For example, a typical element with anti-reflection of 200 to 800 nm and high reflectivity around 1064 nm wavelength has a typical damage threshold of 200-300 $MW/cm^2$ for a typical induced laser pulse with a pulse width of 10 ns and a repetition frequency of 10 Hz, which is hard to reach above 500 $MW/cm^2$. However, the coating technology of the existing high reflectivity devices around 1064 nm wavelength is very mature, the damage threshold may reach to over 2 $GW/cm^2$. Thus, the energy of induced laser of the system will be limited to within a few tens of millijoule, such that the optical element is easily to be damaged. Meanwhile, the element with anti-reflection of 200 to 800 nm and high reflectivity around 1064 nm wavelength is very difficult to coat and has poor effect. For example, the residual reflectance of the element with anti-reflection of 200 to 800 nm and high reflectivity around 1064 nm wavelength anti-reflecting within 200 to 800 nm is 0.5-1.0%, which is 10 to 20 times of that of conventional narrow spectrum range anti-reflection films, whose residual reflectance is 0.05%.

SUMMARY

In view of the above, the objective of the present disclosure is to provide a scanning type laser induced spectrum surface range analysis and detection system, which provides the spectral collection of a wide range of several hundreds of nanometers in a same optical axis, and bears the large energy laser induction in Joule level with an efficiency higher than 90%.

For the above purposes, the canning type laser induced spectrum surface range analysis and detection system provided by the disclosure comprises: a focusing optical device, a reflector, a light collecting device and a laser emitting head; wherein the laser emitting head is connected to an external laser inducing light source, the external laser inducing light source generates lasers emitted through the laser emitting head, so as to generate laser induced plasma; the focusing optical device converges induction excited laser beams emitted by the laser emitting head onto a surface of a tested sample; the reflector collects wide spectral range induced plasma scattered light signals of the tested sample and converges the signals into the light collecting device, the light collecting device converges induced plasma scattered light into an optical fiber and transmits the induced plasma scattered light to an external spectrograph which divides a spectrum formed by the plasma to obtain spectral strength data of different wavelengths.

In some embodiments of the present disclosure, the system further comprises a laser scanning device, wherein the laser scanning device and the focusing optical device converge the induction excited laser beams onto the surface of the tested sample.

The laser scanning device comprises a laser reflector and a laser scanning controller, the laser reflector reflects induced lasers and is coaxial with the focusing optical device; and, the laser scanning controller controls and drives an alignment angle of the laser reflector, so as to converge at different positions of incident induced lasers.

In some embodiments of the present disclosure, the focusing optical device is a lens which converges the induced lasers onto the tested sample; wherein the focusing optical device is a single lens, or a lens set.

In some embodiments of the present disclosure, the focusing optical device further comprises a center-perforated lens on the basis of comprising the lens or lens set; wherein the center-perforated lens and the lens or lens set are sequentially arranged, and the center-perforated lens induces lasers, so as to converges collected plasma scattered light onto the tested sample.

In some embodiments of the present disclosure, the center-perforated lens is a single lens, or a center-perforated lens set.

In some embodiments of the present disclosure, the laser emitting head comprises at least one piece of spherical or aspherical lens, for adjusting divergent angle, facula size, radiation direction and polarization state of lasers emitted from the laser inducing light source.

In some embodiments of the present disclosure, the system comprises a box body, a lens, a center-perforated lens, a laser reflector, a laser scanning controller, a reflector, a light collecting device and a laser emitting head, a tested sample being an alloy metal block that has complex composition.

The box body is a right triangle, a through hole corresponding to the tested sample is formed at an acute angle end of the box body, and the lens, center-perforated lens are arranged in sequence within the box body at the end; two parallel through holes which are provided with the light collecting device and the laser emitting head respectively, are formed at the other acute angle end of the box body; and, the laser scanning controller and the laser reflector connected thereto are provided on a right angle end of the box body, the laser reflector is mounted in a hole on the reflector which is fixed at both ends on inner walls of two right angle sides of the box body.

In some embodiments of the present disclosure, the system comprises a box body, a focusing optical device, a laser reflector, a laser scanning controller, a reflector, a light collecting device and a laser emitting head; wherein the tested sample is a solution that has complex composition.

The box body is polygon, the laser scanning controller and the laser reflector connected thereto are provided on an end angle of the box body, the laser reflector is mounted in a hole on the reflector which is fixed at both ends on two end planes of the box body; and, the focusing optical device is mounted on an end plane of the box body, inside the focusing optical device the lens, center-perforated lens are arranged in sequence; while two parallel through holes which are provided with the light collecting device and the laser emitting head respectively, are formed at the other end plane of the box body.

In some embodiments of the present disclosure, the system comprises a box body, a focusing optical device, a laser reflector, a reflector, a light collecting device and a laser emitting head; the tested sample 9 is a cake-shaped soil sample made by stamping with a trace amount of heavy metal elements.

The box body is polygon, the laser reflector is provided on an end plane of the box body, and the laser reflector is mounted in a hole on the reflector which is fixed to the end plane of the box body; and, the focusing optical device is mounted on an end plane of the box body, inside the focusing optical device the lens and the center-perforated lens are arranged in sequence; while two parallel through holes which are provided with the light collecting device and the laser emitting head respectively, are formed at the other end plane of the box body.

In some embodiments of the present disclosure, the reflector is a spherical mirror or an aspherical mirror, which is optically matched with the light collecting device to converge collected wide spectral range induced plasma scattered light signals of the tested sample into the light collecting device; the laser reflector is plated with a dielectric film or a metal film, which is used for achieving high-efficiency reflection of induced laser of a specific wavelength.

It can be seen from the above that, the scanning type laser induced spectrum surface range analysis and detection system provided by the present disclosure, has high energy loading, and may also be used to provide a scanning type laser induced plasma spectrum detection in a large range. The present disclosure can provide a collection with an efficiency over 90% of extra-wide spectrum signal within a wavelength of 200-1000 nm, by a scanning galvanometer in combination of a paraboloid reflector; and there is no focal point during collecting signals, and no dichroic mirror is needed. Therefore, the system is more mature and reliable in coating; as for the system structure, the structure design with small volume and small size can be provided due to the tight arrangement of the components.

DETAILED DESCRIPTION

In order to clearly specify the objectives, technical solutions, and advantages of the present disclosure, the present disclosure is further described in detail hereinafter with reference to the specific embodiments and accompanying drawings.

Figure 1:
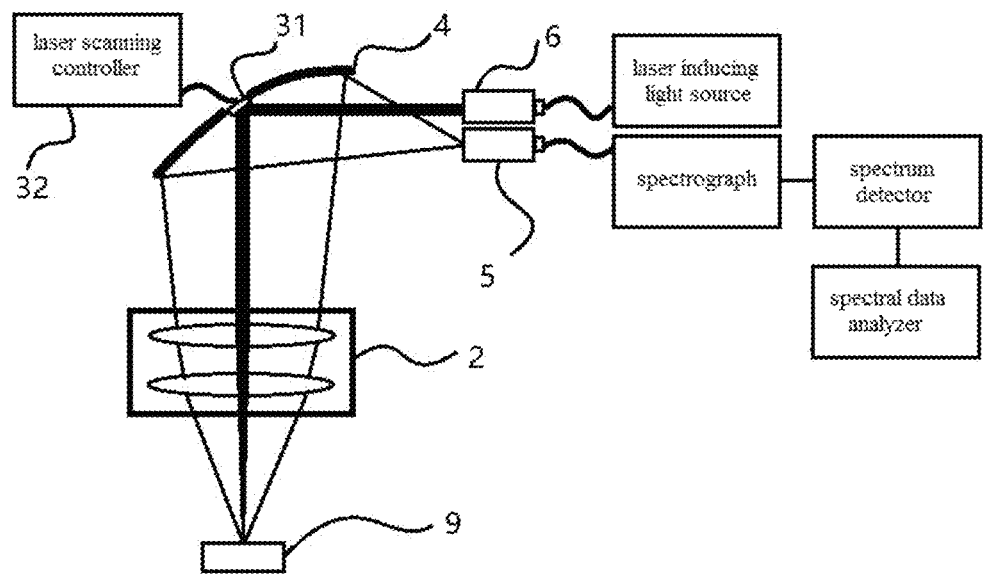
FIG. 1 is a schematic diagram of the scanning type laser induced spectrum surface range analysis and detection system in an embodiment of the present disclosure.

As an embodiment of the present disclosure, as shown in FIG. 1 which is a structure diagram of the scanning type laser induced spectrum surface range analysis and detection system in an embodiment of the present disclosure, the scanning type laser induced spectrum surface range analysis and detection system comprises a focusing optical device 2, a reflector 4, a light collecting device 5 and a laser emitting head 6. Wherein the laser emitting head 6 is connected to an external laser inducing light source, the external laser inducing light source generates lasers emitted through the laser emitting head 6, so as to realize generation of laser induced plasma. The focusing optical device 2 converges induction excited laser beams emitted by the laser emitting head 6 onto a surface of a tested sample 9. Then, the reflector 4 collects wide spectral range induced plasma scattered light signals of the tested sample 9 and converges the signals into the light collecting device 5. The light collecting device 5 converges induced plasma scattered light into an optical fiber and transmits the induced plasma scattered light to an external spectrograph, and the external spectrograph divides a spectrum formed by the plasma to obtain spectral strength data of different wavelengths.

Preferably, the scanning type laser induced spectrum surface range analysis and detection system may further comprise a laser scanning device, the laser scanning device and the focusing optical device 2 converge the induction excited laser beams onto the surface of the tested sample 9. The laser scanning device comprises a laser reflector 31 and a laser scanning controller 32. Wherein the laser reflector 31 reflects induced lasers and is coaxial with the focusing optical device 2. Meanwhile, the laser scanning controller 32 can precisely control and drive the alignment angle of the laser reflector 31 so as to provide the convergence at different positions of incident induced lasers. That is, by the scanning control of the laser scanning controller 32, the scanning over a wide area can be provided so as to realize the scanning type laser induced spectrum analysis.

Preferably, the laser reflector 31 is plated with a dielectric film or a metal film, which is used for achieving high-efficiency reflection of induced laser of a specific wavelength. It also needs to be noted that the laser reflector 31 may be a plane mirror, and it is sufficient to only provide high-efficiency reflection. Of course, the laser reflector 31 may also be a spherical or an aspherical concave mirror, which provides the convergence of induced lasers while achieving the high-efficiency reflection.

Figure 2:
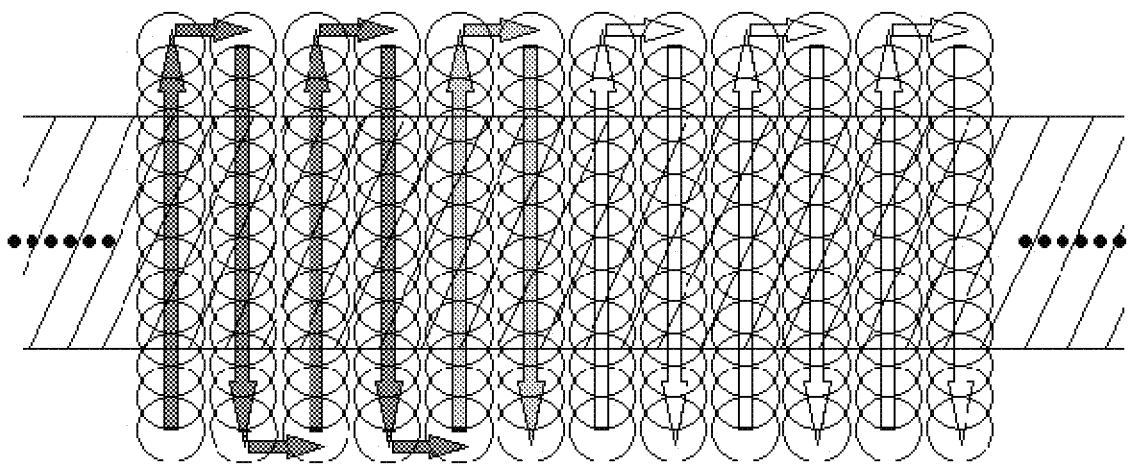
FIG. 2 is a realization approach diagram for scanning type laser induced spectrum surface range analysis and detection in an embodiment of the present disclosure.

In an embodiment, the scanning working modes of the laser scanning device comprise scanning a specific range within a certain section perpendicular to the optical axis of the laser reflector 31 at a certain distance, or scanning within a range along the optical axis at a specific distance. When implementing the working modes of surface scanning, the working plan of scanning is shown in FIG. 2, the laser reflector 31 is controlled by the laser scanning controller 32 so as to realize repetitive induced excitation in a zigzag manner over a surface range, and to realize laser induction detection in a plurality of circular ranges. Through the analysis result data superposition of each point induction detection by an external spectrum detector connected to the external spectrograph, the laser induction detection of the material composition within surface range can be provided, and surface distribution images are obtained with an external spectral data analyzer.

It needs to be noted that the tested sample 9 may be solid, liquid or gas sample, and may be any material capable of generating plasma by laser excitation and performing spectral analysis. It may also be tested materials under the conditions such as in a remote distance, in a vacuum, under the water or under a high pressure.

In another embodiment of the present disclosure, the focusing optical device 2 may be lens 21 achieving converging induced lasers onto the tested sample 9. The lens 21 may be one lens, or may be a lens set with more than 10 lenses. When the lens 21 is a lens set, the convergence characteristics on the material surface of induced lasers may be adjusted by adjusting the lens 21 composed of a plurality of lenses, so as to realize different convergence distances. In an embodiment, the spaces between the lenses of the lens set may be adjusted so as to realize the adjustment of focal positions within a range of 100 mm to 1000 mm, control the ratio of long radius and short radius of elliptical converging spot; adjust the size of circular spot radius.

In addition, the focusing optical device 2 may further comprise a center-perforated lens 22 on the basis of comprising the lens 21. The center-perforated lens 22 and the lens 21 are sequentially arranged, and the center-perforated lens 22 may also induce lasers, so as to converge collected plasma scattered light onto the tested sample 9. Preferably, the center-perforated lens 22 may be one lens, or a center-perforated lens set with up to 10 lenses. Preferably, considering diffraction, the circular hole diameter of the center-perforated lens 22 is 2 mm to 15 mm, which is slightly larger than the diameter of passed lasers. When the center-perforated lens 22 is a center-perforated lens set, the convergence characteristics of the plasma scattered light may be adjusted by adjusting the center-perforated lens 22 composed of a plurality of center-perforated lenses, so as to realize the convergence of the plasma scattered light at different distances.

As an embodiment of the present disclosure, the reflector 4 may be a spherical mirror or an aspherical mirror, which can be optically matched with the light collecting device 5 to converge collected wide spectral range induced plasma scattered light signals of the tested sample 9 into the light collecting device 5. In addition, the reflector 4 is arranged with a hole or has space in the front to place the laser reflector 31, such that the induced lasers reflected by the laser reflector 31 and the collected spectral signal light are in a same axis. Preferably, the reflector 4 may provide high-efficiency reflection by plating metal film (such as aluminum film), dielectric film etc. Preferably, the reflector 4 needs to provide a spectral high-efficiency reflection with a range from tens to hundreds nm, for example, a high-efficiency reflection about 93% within a range of 200-100 nm may be provided by plating aluminum film. In addition, there is an included angle from 5° to 170° between the incident signal light of the reflector 4 and the converged signal light, such as 90° or 30°.

As another embodiment, the light collecting device 5 may be a fiber coupling head formed by a lens set, and reduce the aberration to converge the collected induced plasma scattered light into the optical fiber, and then transmit it to an external spectrograph. Preferably, the light collecting device 5 may include 1 to 10 pieces of lens combination. In addition, the external spectrograph divides the spectrum formed by the plasma to obtain spectral strength data of different wavelengths. The external spectrograph may be a conventional spectrograph with one grating division, which performs the collection of linear distribution through linear array CCD, CMOS, or performs fixed-point spectrum collection through the linear array of elements such as photomultiplier tube etc. The external spectrograph may also be a spectrograph with two (two-dimension) or more dimensions and has wide spectral range and high spectrum resolution, such as middle-ladder grating spectrograph, it performs the collection of linear distribution through linear array CCD, CMOS, or performs fixed-point spectrum collection through the linear array of elements such as photomultiplier tube etc.

Furthermore, the external spectrograph may be connected to a spectrum detector to collect and process divided light signals, so as to form the data curve of wavelength-relative strength. Preferably, the spectrum detector may be a photoelectric one-dimensional detector element which senses light signals, such as photodiode (PD), photomultiplier tube (PMT), avalanche photodiode (APD) etc. It may also be a one-dimensional detector element which senses with pyroelectricity, such as energy meter, power meter, four-quadrant detector etc. It may further be an EmCCD, ICCD, CCD, CMOS, or other charge-coupled sensing detector elements. The spectrum detector may also be a one-dimensional or two-dimensional detecting system composed by the above elements or the arrays thereof. The spectrum detector cooperates with the spectrograph, when the spectrograph is a one-dimensional grating division system, the spectrum detector is provided with linear detection source; when the spectrograph is a two-dimensional grating division system, the spectrum detector is provided with plane detection source. If only the signals with specific wavelength are to be analyzed and processed, the spectrum detector can be provided with point detection source for the one-dimensional grating division system; and the spectrum detector can be provided with point or linear detection source for the two-dimensional grating division system.

In another further embodiment, an external spectral data analyzer connected with the spectrum detector may process the spectral data of wavelength-relative strength, and calculate and analyze to obtain the elementary composition. When the scanning type laser induced spectrum surface range analysis and detection system performs scanning function, the splicing of multiple data needs to be done so as to form a three-dimensional topography of specific element.

As another embodiment, the laser emitting head 6 may comprise 1 to 10 pieces of spherical, aspherical lenses, for adjusting the divergent angle, facula size and radiation direction, polarization state of the lasers emitted from the laser inducing light source. Further, by connecting the optical fiber with the laser inducing light source, the optical fiber transmits induced lasers and performs emission. In addition, by providing a light-transmissive window, the induced lasers can directly irradiate on the laser reflector 31, and then the convergent of the induced lasers on the surface of the detected material can be realized by the focusing optical device 2 to excite the plasma.

In the embodiment, the external laser inducing light source may be one of semiconductor laser, solid or gas laser, such as Nd:YAG laser. It may also be a semiconductor laser which outputs by coupling with optical fiber, or a carbon dioxide laser, it may further be a laser which outputs in pulse, or a laser which outputs continuously. It may also be a laser which is able to output 2 to 100 pulses with adjustable time interval by power source or optical modulation, for continuously exciting plasma on the tested sample 9. In other embodiments, the external laser inducing light source is combined by 2 to 5 lasers, which are controlled by a uniform timing control device, and excite plasma on the material surface according to preset time interval. The excitation effect of the plasma may be improved by outputting multi-wavelength lasers simultaneously or from different light sources, according to excitation demands of the plasma.

Figure 3:
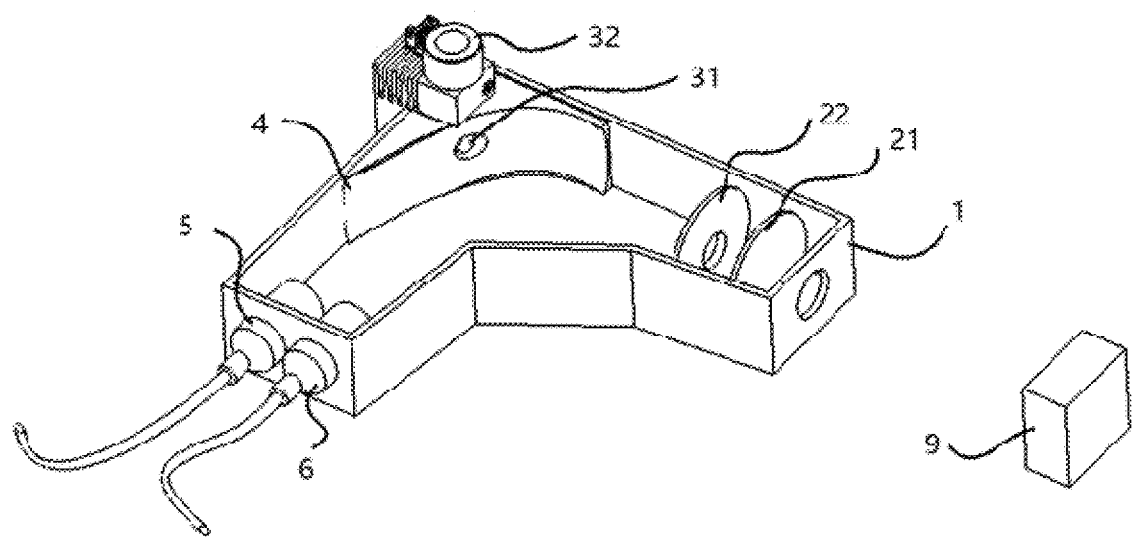
FIG. 3 is a structure diagram of the scanning type laser induced spectrum surface range analysis and detection device in a first referential embodiment of the present disclosure.

In a first referential embodiment of the present disclosure, a laser induced spectrum surface range analysis and detection system that can scan in a coaxial plane, such as the high-efficiency coaxial scanning laser induced spectroscopy device shown in FIG. 3, comprises a box body 1, a lens 21, a center-perforated lens 22, a laser reflector 31, a laser scanning controller 32, a reflector 4, a light collecting device 5 and a laser emitting head 6, a tested sample 9 being an alloy metal block that has complex composition. Wherein the box body 1 is a right triangle, a through hole corresponding to the tested sample 9 is formed at an acute angle end of the box body 1, and the lens 21, center-perforated lens 22 are arranged in sequence within the box body at this end. Two parallel through holes which are provided with the light collecting device 5 and the laser emitting head 6 respectively, are formed at the other acute angle end of the box body 1. Meanwhile, the laser scanning controller 32 and the laser reflector 31 connected thereto are provided on the right angle end of the box body 1, the laser reflector 31 is mounted in a hole on the reflector 4 which is fixed at both ends on the inner walls of two right angle sides of the box body 1.

Preferably, the box body 1 is made of aviation aluminum. The lens 21 is a biconvex spherical lens with a diameter of 50 mm and is coated with an antireflection film having a wide spectrum range. The center-perforated lens 22 is with a diameter of 50 mm, and has a circular hole in the center with a diameter of 15 mm, the center-perforated lens 22 is made of quartz glass and coated with an antireflection film having a wide spectrum range. The laser reflector 31 is a plane reflector having a diameter of 10 mm, and capable of achieving a high-efficiency reflection over 99.5% about the wavelengths of the incident laser. The laser scanning controller 32 is a scanning galvanometer, and capable of rotating within a range of 0 to 2° to realize scanning control of the output lasers. The reflector 4 is a paraboloid reflector with a paraboloid size of 70 mm×200 mm, and capable of turning and converging the incident lasers for 90 degrees, and eliminating aberrations by itself; the laser reflector 31 is placed in a hole with a diameter of 12 mm on the optical axis. The light collecting device 5 is composed of 2 quartz aspherical lenses, is capable of achieving high-efficiency coupling of the signal light in a spectrum range of 200 to 800 nm, the external spectrograph is a middle-ladder grating spectrograph of and or company. The laser emitting head 6 is an optical fiber coupling head, which includes three lenses inside, and the external laser inducing light source generates an induced laser with a pulse width of 10 ns, a center wavelength of 1064 nm, a repetition frequency of 10 Hz and energy of 200 mJ.

Therefore, when the high-efficiency coaxial scanning laser induced spectroscopy device operates, the pulse laser generated by the laser inducing light source emit through the laser emitting head 6, so as to compress the divergent angle, such that the laser becomes near-parallel light with a divergent angle less than 0.5 mrad and a diameter of 6 mm. The induced laser is reflected by the laser reflector 31 at an incidence angle of 45°, after 90° of turning, the induced laser is emitted from the center of the center-perforated lens 22 and converged by the lens 21 on the material surface of the tested sample 9. The pulse laser induces the generation of plasma, and the obtained scattered light is shaped by the lens 21 and the center-perforated lens 22 to be projected on the reflector 4. The reflector 4 converges the projected plasma signal light into the light collecting device 5. The signal light obtained by the light collecting device 5 is processed by the spectrograph, and transmitted to an ICCD detector. The composition of the tested sample 9 is analyzed in combination with a spectral data analyzer.

Meanwhile, during scanning, the laser scanning controller 32 drives the laser reflector 31 to rotate in a two-dimensional direction, the maximum rotation angle is 3°, such that the induced laser has a focal facula with a diameter of 0.1 mm on the surface of the tested material. And each pulse, or consecutive 10 pulses excites in a circular range. Then the laser scanning controller 32 controls the laser reflector 31 to rotate until the scanning is completed in a 60 mm×60 mm range according to the snake-shaped working mode as shown in FIG. 2. Finally, the spectral data analyzer processes the spectral data of wavelength-relative strength, calculates and analyzes to obtain the elementary composition, and then superposes and splices the data of each measurement, so as to form a three-dimensional topography of specific element.

Figure 4:
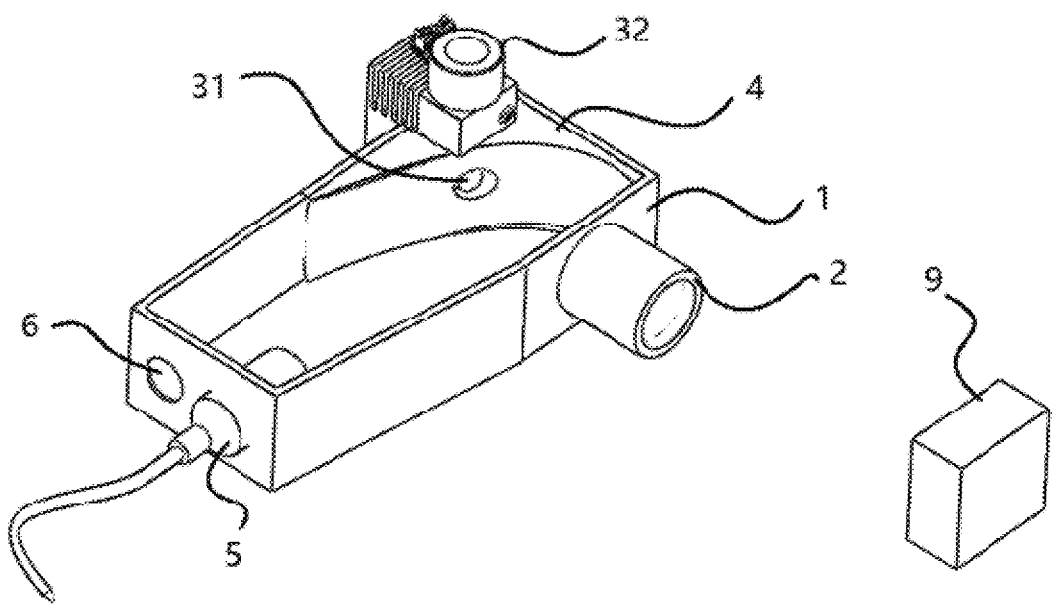
FIG. 4 is a structure diagram of the scanning type laser induced spectrum surface range analysis and detection device in a second referential embodiment of the present disclosure.

In a second referential embodiment of the present disclosure, a scanning type laser induced spectrum surface range analysis and detection system which is highly efficient and bears high power, and scans along an optical axis direction, such as the scanning type laser induced spectrum surface range analysis and detection device shown in FIG. 4, comprises a box body 1, a focusing optical device 2, a laser reflector 31, a laser scanning controller 32, a reflector 4, a light collecting device 5 and a laser emitting head 6. Wherein, the tested sample 9 is a solution that has complex composition. The box body 1 is polygon, the laser scanning controller 32 and the laser reflector 31 connected thereto are provided on an end angle of the box body 1, the laser reflector 31 is mounted in a hole on the reflector 4 which is fixed at both ends on two end planes of the box body 1. Meanwhile, the focusing optical device 2 is mounted on an end plane of the box body 1, inside the focusing optical device 2 the lens 21, center-perforated lens 22 are arranged in sequence. While two parallel through holes which are provided with the light collecting device 5 and the laser emitting head 6 respectively, are formed at the other end plane of the box body 1.

Preferably, the laser emitting head 6 only needs to focus the incident induced laser to the laser reflector 31 directly. Therefore the laser emitting head 6 may be a light-transmissive window which uses the incident laser directly. That is, the induced laser may illuminate on the laser reflector 31 directly through the light-transmissive window of the laser emitting head 6.

Preferably, the box body 1 is made of aviation aluminum. The focusing optical device 2 comprises the center-perforated lens 22 and the lens 21 that are arranged in sequence, the center-perforated lens 22 is with a diameter of 25 mm, and has a circular hole in the center with a diameter of 6 mm, the center-perforated lens 22 is made of quartz glass and coated with an antireflection film having a wide spectrum range. The lens 21 is a biconvex spherical lens with a diameter of 25 mm and is coated with an antireflection film having a wide spectrum range. The focusing optical device 2 is arranged outside the box body 1, and realizes the adjustment of different working distances from the box body 1 to the tested sample 9 manually. The laser reflector 31 is a plane reflector having a diameter of 10 mm, and capable of achieving a high-efficiency reflection over 99.5% about the wavelengths of the incident laser. The laser scanning controller 32 is a scanning galvanometer, and capable of rotating within a range of 0 to 2° to realize scanning pointing direction control of the output lasers. The reflector 4 is a paraboloid reflector with a paraboloid size of 70 mm×200 mm, and capable of turning and converging the incident lasers for 90 degrees, and eliminating aberrations by itself. Meanwhile, the laser reflector 31 is placed in a hole with a diameter of 12 mm on the optical axis of the reflector 4. The light collecting device 5 is composed of 2 quartz aspherical lenses, is capable of high-efficiency coupling of the signal light in a spectrum range of 200 nm to 800 nm, the external spectrograph is a middle-ladder grating spectrograph of and or company. In addition, the laser inducing light source generates an induced laser with a pulse width of 8 ps, a center wavelength of 532 nm, a repetition frequency of 10 Hz, and single pulse energy of 200 μJ, the induced laser illuminates on the laser reflector 31 directly.

Therefore, when the scanning type laser induced spectrum surface range analysis and detection device operates, the pulse laser generated by the laser inducing light source emits through the laser emitting head 6, so as to compress the divergent angle, such that the laser becomes near-parallel light with a divergent angle less than 0.5 mrad and a diameter of 4 mm. The induced laser is reflected by the laser reflector 31 at an incidence angle of 45°, after 90° of turning, the induced laser is emitted from the center of the center-perforated lens 22 and converged by the lens 21 on the material surface of the tested sample 9 which can move back and forth beyond 1000 mm. The pulse laser induces the generation of plasma, and the obtained scattered light is shaped by the lens 21 and the center-perforated lens 22 to be projected on the reflector 4. The reflector 4 converges the projected plasma signal light into the light collecting device 5. The signal light obtained by the light collecting device 5 is processed by the spectrograph, and transmitted to an ICCD detector. The composition of the tested sample 9 is analyzed in combination with a spectral data analyzer. By adjusting the relative position between the center-perforated lens 22 and the lens 21 manually, accurate focusing of the laser and accurate detection of the plasma signal light on the light collecting device 5 can be realized.

Figure 5:
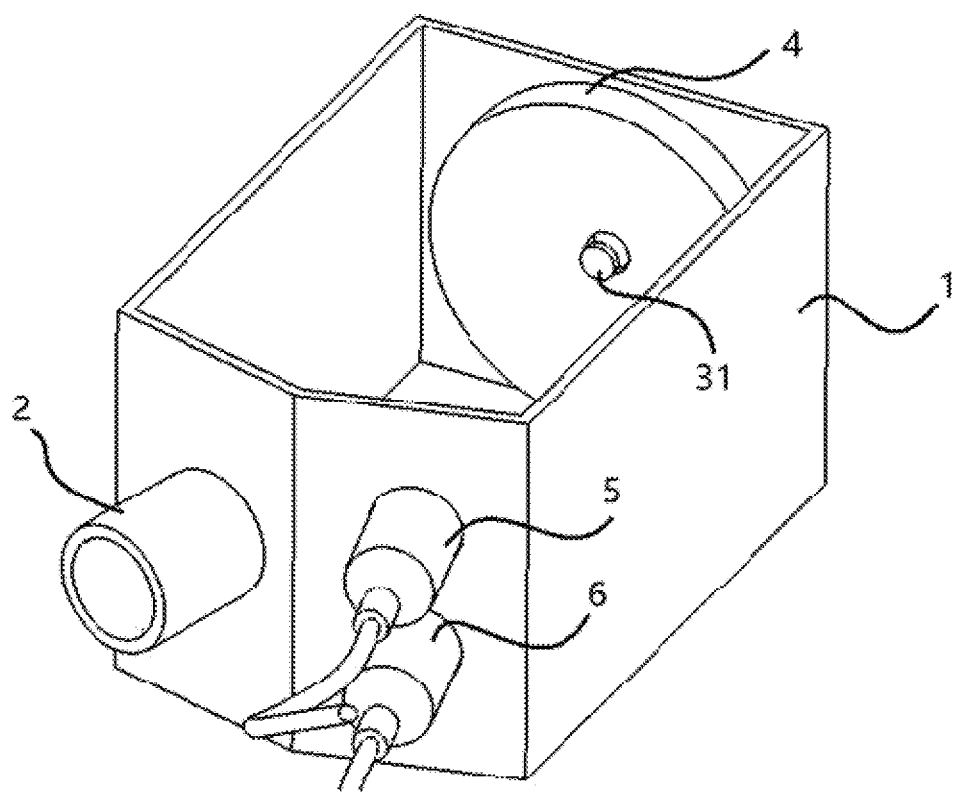
FIG. 5 is a structure diagram of the scanning type laser induced spectrum surface range analysis and detection device in a third referential embodiment of the present disclosure.

In a third referential embodiment of the present disclosure, a scanning type laser induced spectrum surface range analysis and detection system which is highly efficient and bears high power, such as the scanning type laser induced spectrum surface range analysis and detection device shown in FIG. 5, comprises a box body 1, a focusing optical device 2, a laser reflector 31, a reflector 4, a light collecting device 5 and a laser emitting head 6. The tested sample 9 is a cake-shaped soil sample made by stamping with a trace amount of heavy metal elements. Wherein, the box body 1 is polygon, the laser reflector 31 is provided on an end plane of the box body 1, and the laser reflector 31 is mounted in a hole on the reflector 4 which is fixed to the end plane of the box body 1. Meanwhile, the focusing optical device 2 is mounted on an end plane of the box body 1, inside the focusing optical device 2 a lens 21 and a center-perforated lens 22 are arranged in sequence. While two parallel through holes which are provided with the light collecting device 5 and the laser emitting head 6 respectively, are formed at the other end plane of the box body 1.

Preferably, the box body 1 is made from open mold injection molding, so as to meet the shape and stability requirements. The focusing optical device 2 is lens 21, and the lens 21 is composed of two plano-convex spherical lenses with a diameter of 25 mm and coated with an antireflection film having a wide spectrum range. The focusing optical device 2 is arranged outside the box body 1, and realizes the fixation of the working distance from the box body 1 to the tested sample 9. The laser reflector 31 is a concave reflector having a diameter of 10 mm and fixed on the reflector 4 by glue, it is capable of achieving a high-efficiency reflection over 99.5% of a narrow spectral range of 20 nm about the wavelength of the incident laser. The reflector 4 is a concave spherical reflector with a diameter of 80 mm, and has a hole of a diameter of 10.5 mm on the center axis, the laser reflector 31 is glued to the center of the hole. In a simplified batch design scheme, the laser reflector 31 and the reflector 4 can be integrally formed by injection molding, open molding, and stamping, and then a laser reflector 31 is glued to an appropriate position of the reflector 4, The scheme shown in FIG. 5 is that the concave spherical reflector has a hole on the center axis, and the laser reflector 31 is glued. The light collecting device 5 is composed of 1 quartz aspherical lens, is capable of achieving high-efficiency coupling of the signal light in a spectrum range of 200 to 800 nm. In addition, the laser inducing light source is lasers emitted from a small semiconductor laser, with a center wavelength of 1.5 μm, a repetition frequency of 5 Hz, and single pulse energy of 100 mJ, the laser is output through the coupling of optical fiber, and the induced laser illuminates on the laser reflector 31 directly.

Therefore, when the scanning type laser induced spectrum surface range analysis and detection device operates, the pulse laser generated by the laser inducing light source emits through the laser emitting head 6, and the diameter of the facula illuminating onto the laser reflector 31 is about 7 mm, the incidence angle is 15°, after 30° of turning after reflection, the laser is converged on the surface of the material beyond 600 mm by the laser reflector 31 and the focusing optical device 2. The pulse laser induces the generation of plasma, and the obtained scattered light is converged by the focusing optical device 2 and projected on the reflector 4. The reflector 4 converges the projected plasma signal light into the light collecting device 5. The signal light obtained by the light collecting device 5 is processed by the spectrograph, and transmitted to a photomultiplier placed in a specific position. The composition of the tested sample 9 is analyzed in combination with a spectral data analyzer.

Therefore, the scanning type laser induced spectrum surface range analysis and detection system creatively avoids the disadvantage of vulnerability of the dichroic optics in the transmission and reception coaxial laser induced spectrum optical solution; moreover, the scanning mode can be realized, and the scanning type laser induced plasma spectrum detection in a large range can be provided by the scanning galvanometer in combination of defocused parabolic reflector; and there is no focal point during signal collection, therefore axial scanning or area array scanning can be provided. Meanwhile, coaxial emission and collection can ensure a more stable scanning working mode, and can effectively control the signal strength changes caused by the relative position changes; in addition, the optical efficiency of collecting spectrum signal is high, since the wavelength range of the laser is narrow and the reflection angle is small, the laser reflector can provide a reflection efficiency over 99.5%; the reflector 4 may provide a reflection efficiency over 93% within a range of 200-1000 nm through aluminized film, the theoretical efficiency of the new word system is over 90%; a highly effective collection with an efficiency over 90% of extra-wide spectrum signal within hundreds of nanometers spectrum range can be provided; at the same time, as for the system structure, the structure design with small volume and small size can be provided due to the tight arrangement of the components; therefore, the scanning type laser induced spectrum surface range analysis and detection system described by the disclosure has a stable structure, high reliability and excellent practical value.

Those of ordinary skill in the art should understand: the descriptions above are merely specific embodiments of the present disclosure, and are not intended to limit the present disclosure. Any modification, equivalent replacement, improvements and the like made within the spirit and principle of the present disclosure should be included in the protection scope of the present invention.

What is claimed is:

1. A scanning type laser induced spectrum surface range analysis and detection system, comprising: a focusing optical device, a reflector, a light collecting device, a laser emitting head, a box body, and a laser scanning device,
   wherein the laser emitting head is connected to an external laser inducing light source disposed outside of the box body, the external laser inducing light source generates lasers emitted through the laser emitting head, so as to generate laser induced plasma;
   the focusing optical device converges induced excited laser beams emitted by the laser emitting head onto a surface of a tested sample;
   induced plasma scattered light signals of the tested sample are incident on the reflector and the reflector converges the induced plasma scattered light signals into the light collecting device, the light collecting device converges the induced plasma scattered light signals into an optical fiber and transmits the induced plasma scattered light signals to an external spectrograph disposed outside of the box body which divides a spectrum formed by the plasma to obtain spectral strength data of different wavelengths;
   wherein the laser scanning device and the focusing optical device converge the induction excited laser beams onto the surface of the tested sample; the laser scanning device comprises a laser reflector and a laser scanning controller, the laser reflector reflects induced lasers and is coaxial with the focusing optical device; and the laser scanning controller controls and drives an alignment angle of the laser reflector, so as to converge incident induced lasers at different positions;
   wherein the focusing optical device is a lens which converges the induced lasers onto the tested sample; and the focusing optical device is a single lens, or a lens set; and
   wherein the focusing optical device further comprises a center perforated lens; and the center perforated lens and the lens or lens set are sequentially arranged, and the induced lasers are emitted from the center perforated lens, so as to converge on the surface of the tested sample.

2. The system of claim 1, wherein the center-perforated lens is a single lens or a center-perforated lens set.

3. The system of claim 1, wherein the laser emitting head comprises at least one piece of spherical or aspherical lens, for adjusting divergent angle, facula size, radiation direction and polarization state of lasers emitted from the laser inducing light source.

4. The system of claim 1, further comprising the box body, wherein the box body is a right triangle, a through hole corresponding to the tested sample is formed at an acute angle end of the box body, and the lens, center-perforated lens are arranged in sequence within the box body at the end; two parallel through holes which are provided with the light collecting device and the laser emitting head respectively, are formed at the other acute angle end of the box body; and, the laser scanning controller and the laser reflector connected thereto are provided on a right angle end of the box body, the laser reflector is mounted in a hole on the reflector which is fixed at both ends on inner walls of two right angle sides of the box body.

5. The system of claim 1 further comprising the box body, wherein the box body is polygon, the laser scanning controller and the laser reflector connected thereto are provided on an end angle of the box body, the laser reflector is mounted in a hole on the reflector which is fixed at both ends on two end planes of the box body; and, the focusing optical device is mounted on an end plane of the box body, inside the focusing optical device the lens, center-perforated lens are arranged in sequence; while two parallel through holes which are provided with the light collecting device and the laser emitting head respectively, are formed at the other end plane of the box body.

6. The system of claim 1, further comprising the box body, wherein the box body is polygon, the laser reflector is provided on an end plane of the box body, and the laser reflector is mounted in a hole on the reflector which is fixed to the end plane of the box body; and, the focusing optical device is mounted on an end plane of the box body, inside the focusing optical device the lens and the center-perforated lens are arranged in sequence; while two parallel through holes which are provided with the light collecting device and the laser emitting head respectively, are formed at the other end plane of the box body.

7. The system of claim 1, wherein the reflector is a spherical mirror or an aspherical mirror, which is optically aligned with the light collecting device to converge the induced plasma scattered light signals of the tested sample into the light collecting device; and the laser reflector is plated with a dielectric film or a metal film, which provides high-efficiency reflection of induced laser of a specific wavelength.

* * * * *